United States Patent [19]

Albright et al.

[11] 4,041,012
[45] Aug. 9, 1977

[54] ACRYLATE ESTERS OF DIHALONEOPENTYL GLYCOL PHOSPHATES (PHOSPHORINANES) AND THEIR USE AS FLAME RETARDANTS

[75] Inventors: James A. Albright; Michael W. Lindvay, both of Ann Arbor, Mich.

[73] Assignee: Velsicol Chemical Corporation, Chicago, Ill.

[21] Appl. No.: 691,533

[22] Filed: June 1, 1976

[51] Int. Cl.² .................... C07F 9/06; C08K 5/52; C08L 37/00
[52] U.S. Cl. ................. 260/45.8 A; 260/45.7 P; 260/45.7 S; 260/937; 526/266; 526/275
[58] Field of Search ........... 260/45.7 P, 937, 45.8 A, 260/927 R; 526/266, 275

[56] References Cited

U.S. PATENT DOCUMENTS

| | | | |
|---|---|---|---|
| 3,463,837 | 8/1969 | Friedman | 260/45.7 P |
| 3,887,656 | 6/1975 | Shim | 260/937 |
| 3,962,377 | 6/1976 | Spivack | 260/927 R |

OTHER PUBLICATIONS

DOS 2,262,336, 6/28/1973, Kyung Sup Shim.

*Primary Examiner*—H.S. Cockeram
*Attorney, Agent, or Firm*—Robert M. Phipps

[57] ABSTRACT

Novel compounds of the formula

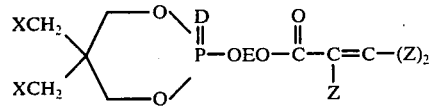

wherein each X is halogen, E is a lower alkylene group containing from about 2 to about 4 carbon atoms, D is chalcogen and each Z is independently selected from the group consisting of hydrogen and alkyl groups containing from 1 to about 4 carbon atoms. The above compounds are effective reactive flame retardants in acrylic polymeric compositions.

14 Claims, No Drawings

ACRYLATE ESTERS OF DIHALONEOPENTYL GLYCOL PHOSPHATES (PHOSPHORINANES) AND THEIR USE AS FLAME RETARDANTS

BACKGROUND OF THE INVENTION

1. Field of the Invention

This invention relates to compounds which are acrylate esters of dihaloneopentyl glycol phosphates. The compounds of this invention are reactive flame retardants for acrylic polymeric compositions.

2. Description of the Prior Art

During the past several years, a large number of flame retardants have been developed for use with an almost equally large number of flammable materials. Cellulosic materials such as paper and wood and polymeric materials such as polyolefins, polyurethane, and polystyrene are just two examples of materials for which flame retardants have been developed. For any class of flammable materials, such as synthetic type polymers, those skilled in the art have long been aware that some flame retardant additives are more effective in polymers and polymeric compositions than other flame retardant additives. This is because the efficacy of any flame retardant in polymers or polymeric compositions is measured not only by the flame retardant capability of the additive but also by the ability of the additive to improve or modify, or at least not to detract from, other physical or mechanical properties of the polymer or polymeric composition. The mere fact, therefore, that most flame retardants contain halogen and phosphorus atoms does not assure that any given halogenated or phosphorus-containing compound will impart usable flame retarding characteristics to all or even to any polymeric system.

The prior art has specifically recognized the problems of finding suitable flame retardants for various resins in view of the fact that polymer systems differ substantially in both flammability characteristics and physical properties and there is no predictability whatsoever from one system to another. Thus in the Norris et al paper entitled "Toxicological and Environmental Factors Involved in the Selection of Decabromodiphenyl Oxide as a Fire Retardant Chemical", Applied Polymer Symposium No. 22, 195-219 (1973), the authors state: "A growing recognition of the huge annual toll taken by fire is resulting in more stringent flammability requirements for synthetic polymers in a variety of applications. Because of economic constraints and the need to produce flame resistant polymers without total replacement of existing manufacturing processes, increased flame resistance is generally achieved by incorporation of a fire retardant chemical in the finished product. This chemical is usually based on bromine, chlorine, phosphorus, or nitrogen and may either be chemically reacted or physically blended into the product. Since polymer systems differ markedly in both flammability characteristics and physical properties, selection of a suitable flame retardant depends on a variety of factors that severely limits the number of acceptable materials."

The resultant disadvantages in the utilization of various prior art materials as flame retardants, in general, for plastic compositions include, without limitation, factors such as thermal migration, heat instability, light instability, non-biodegradability, toxicity, discoloration, the large amounts employed in order to be effective, and the unpredictable end results obtained when using the same material in different plastics (note, for example, in Modern Plastics Encyclopedia, Vol. 49, No. 10A, October, 1972, page 650, wherein octabromobiphenyl is suitable for use in polyolefins as a flame retardant thereof, but is not shown for use (or functionally equivalent) as such for the other 27 compositions listed such as ABS; polycarbonates, polystyrene, acrylics and polyurethanes). Thus, it can be seen that the field of flame retardancy is highly sophisticated and consequently requires substantial research effort to achieve a particular desired end result.

In conjunction with the foregoing discussion, the prior art in general suggests the use of halogen-containing materials as "potential" or "possible" flame retardants for plastic materials. However, the prior art also recognizes that any material must be adjudged on a case by case basis because of the unpredictable results of the end product when any additive is incorporated therein. For example, with reference to the use of a halogenated fire retardant in U.S. Pat. No. 3,658,634 attention is directed to the fact that the patentee specifically points out the disadvantages in the use of a halogen-containing fire retardant. In Column 1, lines 14-17, the patentee states: "Therefore, if it is possible to impart fire-retardancy to the thermoplastic polymers without deteriorating the useful properties of the thermoplastic polymers, they can be widely used in the field of inertia, construction and electric industries." In Column 1, lines 26-32 the patentee states: "--the compounds containing chlorine or bromine atoms to be used as fire-retardant agents, are generally sublimated and therefore, the fire retardant agents are sublimated and lost in the process for producing fire-retardant polymers or in afterfinishing processes; accordingly, deteriorations of fire-retardancy or difficulties in use tend to occur more often than not."

In column 1, lines 29-44 the patentee states: "--the compounds containing chlorine or bromine atoms to be used as fire-retardant agents are unstable in most cases when exposed to ultraviolet rays." In Column 1, lines 59-64 the patentee states: "However, as a matter of fact, only very few fire-retardant polymers can be used in actual practice although they are said to have fire-retardant effects, because there are restrictions such as the conditions employed in production attributable to the properties of the fire-retardant agent, or to the properties of the polymers into which they are to be incorporated."

It can be seen, then, from the foregoing discussion and quoted subject matter that the field of flame retardancy is highly sophisticated, unpredictable and requires substantial research to produce an end product (plastic composition) which meets the necessary criteria for utilitarian purposes, particularly under the present day government standards. Thus, there is always a demand for a material which will function as a flame retardant in an acrylic resin and concurrently will not, by incorporation therein, adversely affect the chemical and/or physical and/or mechanical properties of the resultant acrylic resin plastic composition and also have utility.

The complexity of the foregoing situation is illustrated by a brief consideration of the patent literature. In U.S. Pat. No. 2,899,455 there is disclosed a group of aldehyde derivatives of 2,2-dimethyl-1,3-propanediol cyclic hydrogen phosphite which are mentioned as useful as pesticides, plasticizers, solvents, flame proofing agents and intermediates, yet the only elucidated use is that of a pesticide. A later German patent publication, 2,262,336, discloses halogenated neopentylglycol-phosphate esters of organic hydroxy compounds as flame retardants for flexible polyurethane foams and thermoplastic fibers such as poly(ethyleneterphthalate). However, these esters are substantially nonreactive in polymerization reactions of the acrylic acid type and therefore must be classified as additive in nature. A still later patent, U.S. Pat. No. 3,890,409, discloses spirophosphate aromatic ethers which are useful as additive flame retardants.

Balancing all of the foregoing considerations and thereby developing polymeric compositions with good flame retardant characteristics as well as a satisfactory balance of other properties is, consequently a task which has in the past and presently continues to require the exercise of a high degree of inventive skill.

SUMMARY OF THE INVENTION

In accordance with this invention there are provided acrylate esters of dihaloneopentyl phosphates of the formula:

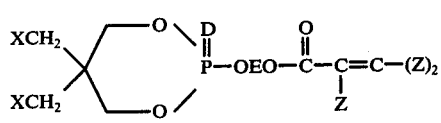
(I)

wherein each X is halogen, E is a lower alkylene group containing from about 2 to about 4 carbon atoms, D is chalcogen and each Z is independently selected from the group consisting of hydrogen and alkyl groups containing from 1 to about 4 carbon atoms per group. Also, an acrylic polymeric composition comprising an acrylic polymer and a flame retarding amount of the above described compounds.

DESCRIPTION OF THE PREFERRED EMBODIMENTS

Compounds within the scope of this invention have formula I above. Each X is halogen and preferably each X is independently selected from chlorine and bromine. It is also preferred that all X's be identical. E is a lower alkylene group containing from about 2 to about 4 carbon atoms, preferably 2 carbon atoms. E can be either a straight chain or branched lower alkylene group. Each Z is independently selected from the group consisting of hydrogen and alkyl groups, said alkyl groups containing from 1 to about 4 carbon atoms per group. Preferably, each Z is independently selected from the group consisting of hydrogen and methyl radicals. D is a chalcogen, preferably oxygen or sulfur. For the purposes of illustration only, Table I is designed to further help describe the compounds of formula I and is neither meant nor should it be taken to be a complete listing of all the compounds within the scope of this invention.

The numerical designation used in naming the compounds of this invention can be ascertained by reference to the following formula wherein the members of the heterocyclic ring are numbered.

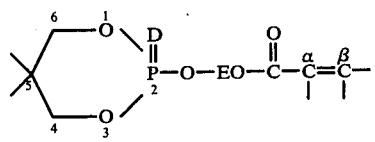

Exemplary compounds are: 2-(methacryloxyethoxy)-5,5-bis(bromomethyl)-2-oxo-1,3,2-dioxaphosphorinane.

The following is a partial listing of preferred compounds

TABLE I

| Compound | X | X | E | $Z^1$ | $Z^2$ | $Z^3$ |
|---|---|---|---|---|---|---|
| When D is Oxygen | | | | | | |
| 1 | Br | Br | —CH₂CH₂— | —CH₃ | H | H |
| 2 | Br | Br | —CH₂CH₂— | H | H | H |
| 3 | Cl | Cl | —CH₂CH₂— | —CH₃ | H | H |
| 4 | Cl | Cl | —CH₂CH₂— | H | H | H |
| 5 | Br | Cl | —(CH₂)₄— | —CH₃ | H | H |
| 6 | Br | Br | —(CH₂)₃— | H | H | H |
| 7 | Cl | Cl | —CH₂CH(CH₃)— | —(CH₂)₃CH₃ | H | —CH₃ |
| 8 | Br | Br | —CH₂CH(CH₃)CH₂— | H | H | H |
| 9 | Cl | Br | —CH₂CH₂— | H | —CH₂CH(CH₃)CH₃ | H |
| 10 | Br | Br | —(CH₂)₃— | —CH₃ | —CH₃ | —CH₃ |
| When D is Sulfur | | | | | | |
| 11 | Br | Br | —CH₂CH₂— | H | H | H |
| 12 | Br | Br | —CH₂CH₂— | —CH₃ | H | H |
| 13 | Cl | Cl | —CH₂CH₂— | —CH₃ | H | H |
| 14 | Cl | Cl | —CH₂CH₂— | H | H | H |
| 15 | Br | Cl | —(CH₂)₄— | —CH₃ | H | H |
| 16 | Br | Br | —(CH₂)₃— | —CH₃ | H | H |
| 17 | Cl | Cl | —CH₂CH₂— | —(CH₂)₃CH₃ | H | —CH₃ |
| 18 | Br | Br | —CH₂CH(CH₃)CH₂— | H | H | H |
| 19 | Cl | Br | —CH₂CH₂— | H | —CH₂CH(CH₃)CH₃ | H |

TABLE I-continued $$\text{XCH}_2\diagdown\diagup\text{O}\diagdown\underset{\|}{\overset{\text{D}}{\text{P}}}-\text{OEO}-\underset{}{\overset{\text{O}}{\underset{\|}{\text{C}}}}-\underset{Z^1}{\overset{}{\text{C}}}=\text{C}\diagup^{Z^2}\diagdown_{Z^3}$$
$$\text{XCH}_2\diagup\diagdown\text{O}\diagup$$

| Compound | X | X | E | $Z^1$ | $Z^2$ | $Z^3$ |
|---|---|---|---|---|---|---|
| 20 | Br | Br | —CH$_2$—CH—<br>        \|<br>        CH$_3$ | —CH$_3$ | —CH$_3$ | —CH$_3$ | within the scope of this invention: 2-(methacryloxyethoxy)-5,5-bis(bromomethyl)-2-oxo-1,3,2-dioxaphosphorinane; 2-(acryloxyethoxy)-5,5-bis(bromomethyl)-2-oxo-1,3,2-dioxaphosphorinane; 2-(methacryloxyethoxy)-5,5-bis(chloromethyl)-2-oxo-1,3,2-dioxaphosphorinane; 2-(acryloxyethoxy)-5,5-bis(chloromethyl)-2-thio-1,3,2-dioxaphosphorinane; 2-(methacryloxyethoxy)-5,5-bis(bromomethyl)-2-thio-1,3,2-dioxaphosphorinane; 2-(acryloxyethoxy)-5,5-bis(bromomethyl)-2-thio-1,3,2-dioxaphosphorinane; 2-(methacryloxyethoxy)-5,5-bis(chloromethyl)-2-thio-1,3,2-dioxaphosphorinane and 2-(acryloxyethoxy)-5,5-bis(chloromethyl)-2-oxo-1,3,2-dioxaphosphorinane.

Compounds within the scope of this invention are prepared according to the general reaction scheme:

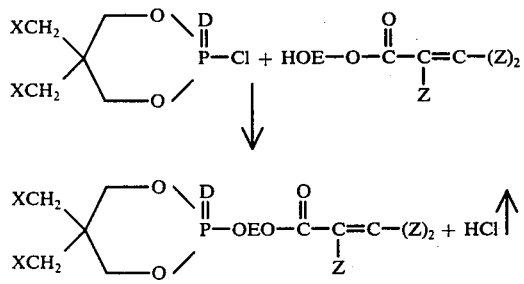

wherein X, D, E and Z are as defined above. In general, equal molar amounts of 5,5-bis(halomethyl)-2-oxo-2-halo-1,3,2-dioxaphosphorinane or 5,5-bis(halomethyl)-2-thio-2-halo-1,3,2-dioxaphosphorinane and the desired acryloxyalkanol are reacted at a temperature of from about 0° to about 120° C. until the theoretical amount of hydrogen chloride is evolved. The reaction can be carried out in the presence or absence of the solvent. Exemplary solvents include benzene, toluene, and chloroform. Catalytic quantities of a metal salt or oxide such as magnesium oxide, magnesium chloride, calcium oxide, calcium chloride, titanium chloride, or vanadium acetate, or stoichiometric quantities of an organic base such as pyridine or triethylamine, can be used to accelerate the completion of the reaction.

Depending on the physical condition of the final end product various product purification and isolation procedures can be used. In the case of a liquid final product, said liquid product is washed with aqueous ammonia to remove any residual acidity. The aqueous ammonia wash is followed by a water wash. The washed product is dried by standard techniques, e.g., at a temperature of from about 100° to about 130° C. until constant weight is achieved.

When a solid product is obtained, said solid product can be purified by washing or recrystallization by techniques which are well known to those skilled in the art, e.g., the solid product can be washed with water or organic solvents such as benzene, toluene, methanol, ethanol, etc., or crystallized from said solvent. The purified solid product is then dried by standard techniques, e.g., at a temperature from about 50° to about 150° C. until constant weight is achieved.

The acrylate ester dihaloneopentyl glycol phosphates of this invention as well as mixtures thereof are useful as flame retardants when in combination with any acrylic polymeric composition. The acrylic polymers with which the flame retardants of this invention can be combined include, but are not limited to, homopolymers of ethyl acrylate, methyl methacrylate, acrylamide, benzyl acrylate, methyl acrylate, butyl methacrylate, etc., copolymers of two or more acrylic monomers and copolymers of one or more such acrylic monomers with other copolymerizable nonacrylic monomers, e.g., acrylonitrile/methacrylate copolymers, butyl methacrylate/glycidyl methacrylate/methacrylic acid terpolymer, acrylonitrile/butadiene/styrene terpolymer, etc. Acrylic homopolymers are the preferred class of acrylic polymeric compositions which can be used with the flame retardants of formula I, with poly(methyl methacrylate) being the most preferred. A further description of acrylic polymers applicable to the present invention may be found in Modern Plastics Encyclopedia, Vol. 52, No. 10A, McGraw-Hill, Inc., New York, New York (1975); Encyclopedia of Polymeric Science and Technology, Vol. I, Inter-science Publishers, John Wiley and Sons, Inc., New York, New York (1964); E. H. Riddle, Monomeric Acrylic Esters, Reinhold Publishing Corp., New York, New York (1954); M. B. Horn, Acrylic Resins, Reinhold Publishing Corp., New York, New York (1960). and J. Brandrop and E. H. Immergut, Polymer Handbook, Second Edition, Wiley Inter-science, New York, New York (1975), said publications being incorporated herein in toto by reference. It is also contemplated that the acrylate ester dihaloneopentyl glycol phosphates of this invention will also possess flame retardant efficacy in polystyrene, unsaturated polyesters and polyacrylonitrile.

It is an advantage of this invention that the present flame retardants can be reacted with unsaturated monomers and thereby be incorporated into the acrylic polymeric composition backbone by copolymerization techniques which are also standard or known to those skilled in the art to provide permanent non-fugutive flame retardancy. (Further examples of the addition reaction technique can be found in W. R. Sorenson and T. W. Campbell, Preparative Methods of Polymer Chemistry, Second Edition, Inter-science Publishers, New York, New York (1968) which is incorporated herein by reference.) Being bound into, or reacted into, the backbone of the polymer chain the flame retardant phosphates of this invention are not subject to solvent extraction or migration due to differences in vapor pressure, reaction to sunlight or other chemical influences. Additionally because the flame retardants of this invention become an integral part of the polymer there is no significant change in physical properties such as is typically experienced by the use of additive type flame retardants, particularly when used in large amounts. Because reactivity rate of the flame retardant of this invention is substantially balanced with that of the acrylate monomer/polymer preparation of the desired flame retarded polymer is easily achieved. Most alkenyl compounds have reactivity rates, i.e., polymerization rates, which are considerably different. A high disparity between reactivity rates would require drastic conditions to cause copolymerization and these are both technically impractical and uneconomical.

The flame retardants within the scope of this invention may additionally be incorporated into or applied onto the above polymers by techniques which are standard or known to those skilled in the art as described, for example, in J. M. Lyons, "The Chemistry and Use of Fire Retardants", Wiley Interscience, New York (1970) or Z. E. Jolles, "Bromine and Its Compounds", Academic Press, New York (1966).

The amount of flame retardant which is used in the compositions and in the methods of this invention is that amount necessary to produce measurable flame retardancy in the compositions which are so modified. Depending upon the particular compound and the particular polymer with which it is combined, the quantity of flame retardant employed in the compositions and methods of this invention can be from about 0.5 to about 35 percent or more by weight of the total composition. For most compositions, a flame retardant will comprise from about 1 to about 25 percent by weight of the total composition.

In addition to the flame retardant compounds within the scope of this invention, the flame retardancy of a polymer such as polystyrene can be further enhanced through the use of so called "synergists" or enhancing agents which, when used with the compounds of formula I, promote a cooperative effect therebetween and thus enhance the flame retardancy of the resultant plastic composition as compared to the flame retardancy of either one component used separately. These "enhancing agents" comprise the oxides and halides of groups IVA and VA of the Periodic Table, and are further described in Modern Plastics Encyclopedia, ibid., as well as U.S. Pat. Nos. 2,993,924; 2,996,528; 3,205,196 and 3,878,165. Without limitation, preferred enhancing agents include $Sb_2O_3$, $SbCl_3$, $SbBr_3$, $SbI_3$, $SbOCl$, $As_2O_3$, $As_2O_5$, $ZnBO_4$, $BaB_2O_4.H_2O$, $2.ZnO.3B_2O_3.3.5H_2O$ and stannous oxide hydrate. The more preferred enhancing agent is antimony trioxide. The enhancing agent can be employed in concentrations as high as 30% by weight of the total composition, preferably up to 15%, and more preferably up to 10%, by weight of the total composition. One level of synergist which is often used is an amount which is from about 25 to about 75%, preferably from about 33 to 67%, by weight of the flame retardant phosphates described above.

It is also within the scope of the present invention to employ other materials in the present invention compositions where one so desires to achieve a particular end result. Such materials include, without limitation, adhesion promoters; antioxidants; antistatic agents; antimicrobials; colorants; heat stabilizers; light stabilizers; pigments; plasticizers; preservatives; ultraviolet stabilizers and fillers. The above mentioned materials, including filler, are more fully described in Modern Plastics Encyclopedia, ibid., and which publication has been incorporated herein in toto by reference.

The following examples are provided for the purpose of further illustration only and are not intended to be limitations on the disclosed invention. Unless otherwise specified, all temperatures are expressed in degrees centigrade; all weights are expressed in grams; and all volumes are expressed in milliliters.

EXAMPLE 1

Preparation of 2-(methacryloxyethoxy)-5,5-bis(-bromomethyl)-2-oxo-1,3,2-dioxaphosphorinane (compound 1 of Table I):

5,5-bis(bromomethyl)-2-chloro-2-oxo-1,3,2-dioxaphosphorinane (172 grams) was dissolved in 400 ml. of benzene and 65 grams of hydroxyethyl methacrylate was added along with 0.1 grams hydroquinone. The solution was cooled in ice and 50 grams of triethylamine was added dropwise with cooling to keep the temperature below 10° C. After complete addition, the temperature was raised to 45° C. for two hours. After cooling and filtering, the benzene solution was washed three times with 300 ml. of water, dried and concentrated. A viscous liquid (142 grams) resulted which was identified by IR and NMR.

In a similar manner other compounds within the scope of this invention, e.g., 2-(acryloxyethoxy)-5,5-(bromomethyl)-2-oxo-1,3,2-dioxaphosphorinane; 2-(methacryloxyethoxy)-5,5-bis(chloromethyl)-2-oxo-1,3,2-dioxaphosphorinane, and 2(-acryloxyethoxy)-5,5-bis(-chloromethyl)-2-oxo-1,3,2-dioxaphosphorinane, can be prepared.

EXAMPLE 2

By using the procedure of Example 1 but substituting an equivalent amount of 5,5-bis(bromomethyl)-2-chloro-2-thio-1,3,2-dioxaphosphorinane for the phosphorus containing compound, 2-(methacryloxyethoxy)-5,5-bis(bromomethyl)-2-thio-1,3,2-dioxaphosphorinane can be prepared.

In a similar manner other compounds within the scope of this invention, e.g., 2-(acryloxyethoxy)-5,5-bis(bromomethyl)-2-thio-1,3,2-dioxaphosphorinane; 2-(methacryloxyethoxy)-5,5-bis(chloromethyl)-2-thio-1,3,2-dioxaphosphorinane and 2-(acryloxyethoxy)-5,5-bis-(chloromethyl)-2-thio-1,3,2-dioxaphosphorinane, can be prepared.

EXAMPLE 3

Benzoyl peroxide (0.12 weight percent) was added to methyl methacrylate syrup (Swedlow, Inc. brand methyl methacrylate, Swedlow, Inc., Garden Grove, California). The flame retardant of Example 1 (25 weight percent) was mixed into the syrup to form a homogeneous solution. The solution was placed in an 8 dram bottle, flushed with nitrogen, and recapped and sealed. The mixture was heated for about 17 hours at 60° C., followed by an additional heating of 1.5 hours at 110° C. The samples were cylindrical sections with a radius of three-eighths of an inch by three inches long. The poly(methyl methacrylate) samples were cut into test species ⅛ of an inch by ⅜ of an inch by three inches. The specimen was tested according to the procedure given by ASTM D-635-72 for flame conditions, draft conditions, and specimen configuration. The specimens were SE (self extinguishing as defined in that test) in 55 seconds after removal of the flame source. A control specimen prepared in the same manner having no flame retardant burned unabatedly after removal of the flame source.

An additional specimen was prepared having a flame retardant load level of 30 weight percent. When tested in the same manner the specimens were SE (self extinguishing) in 2 seconds after removal of the flame source.

The data clearly indicates the compounds within the scope of this invention, as exemplified by Example 1, possess excellent flame retardant efficacy in acrylic polymers, as exemplified by poly(methyl methacrylate). Exemplary flame retardants within the scope of formula I which also display excellent flame retardant efficacy in acrylic polymers include 2-(acryloxyethoxy)-5,5-bis(bromomethyl)-2-oxo-1,3,2-dioxaphosphorinane; 2-(methacryloxyethoxy)-5,5-bis(chloromethyl)-2-oxo-1,3,2-dioxaphosphorinane and 2-(acryloxyethoxy)-5,5-bis(chloromethyl)-2-thio-1,3,2-dioxaphosphorinane.

Based on this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. A compound of the formula

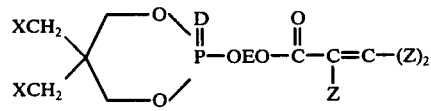

wherein each X is halogen, E is a lower alkylene group containing from about 2 to about 4 carbon atoms, D is chalcogen and each Z is independently selected from the group consisting of hydrogen and alkyl groups containing from about 1 to about 4 carbon atoms per group.

2. The compound of claim 1 wherein each X is independently selected from the group comprising chlorine and bromine.

3. The compound of claim 2 wherein E is a lower alkylene group containing about 2 carbon atoms and wherein each Z is independently selected from the group consisting of hydrogen and methyl radicals.

4. The compound of claim 2 wherein both X's are identical.

5. The compound of claim 1 wherein D is oxygen or sulfur.

6. The compound of claim 5 wherein D is oxygen.

7. The compound of claim 1 selected from the group comprising 2-(methacryloxyethoxy)-5,5-bis(bromomethyl)-2-oxo-1,3,2-dioxaphosphorinane; 2-(acryloxyethoxy)-5,5-bis(bromomethyl)-2-oxo-1,3,2-dioxaphosphorinane; 2-(acryloxyethoxy)-5,5-bis(chloromethyl)-2-oxo-1,3,2-dioxaphosphorinane; and 2-(methacryloxyethoxy)-5,5-bis(bromomethyl)-2-thio-1,3,2-dioxaphosphorinane.

8. An acrylic polymeric composition comprising an acrylic polymer and a flame retarding amount of the compound of claim 1.

9. The acrylic polymeric composition of claim 8 wherein each X is independently selected from the group comprising chlorine and bromine.

10. The acrylic polymeric composition of claim 9 wherein both X's are identical.

11. The acrylic polymeric composition of claim 8 wherein E is a lower alkylene group containing about 2 carbon atoms, and each Z is independently selected from the group consisting of hydrogen and methyl radicals.

12. The acrylic polymeric composition of claim 8 wherein D is oxygen or sulfur.

13. The acrylic polymeric composition of claim 12 wherein D is oxygen.

14. The acrylic polymeric composition of claim 8 wherein the compound is selected from the group comprising 2-(methacryloxyethoxy)-5,5-bis(bromomethyl)-2-oxo-1,3,2-dioxaphosphorinane; 2-(acryloxyethoxy)-5,5-bis(bromomethyl)-2-oxo-1,3,2-dioxaphosphorinane; 2-(methacryloxyethoxy)-5,5-bis(chloromethyl)-2-oxo-1,3,2-dioxaphosphorinane and 2-(methacryloxyethoxy)-5,5-bis(bromomethyl)-2-thio-1,3,2-dioxaphosphorinane, and where the acrylic polymer is poly(methylmethacrylate).

* * * * *